United States Patent
Svaasand et al.

(10) Patent No.: US 6,669,688 B2
(45) Date of Patent: Dec. 30, 2003

(54) METHOD AND APPARATUS FOR MEASURING THE HEAT TRANSFER COEFFICIENT DURING CRYOGEN SPRAY COOLING OF TISSUE

(75) Inventors: Lars O. Svaasand, Trondheim (NO); J. Stuart Nelson, Laguna Niguel, CA (US); Michael W. Berns, Bonsall, CA (US); Sol Kimel, Haifa (IL)

(73) Assignee: The Regents of the University of California, Oakland, CA (US)

( * ) Notice: Subject to any disclaimer, the term of this patent is extended or adjusted under 35 U.S.C. 154(b) by 40 days.

(21) Appl. No.: 09/768,641

(22) Filed: Jan. 23, 2001

(65) Prior Publication Data

US 2002/0123745 A1 Sep. 5, 2002

Related U.S. Application Data

(60) Provisional application No. 60/178,529, filed on Jan. 25, 2000, and provisional application No. 60/208,455, filed on May 31, 2000.

(51) Int. Cl.[7] .............................................. A61B 18/18
(52) U.S. Cl. .......................................... 606/20; 606/22
(58) Field of Search ....................... 62/63, 98; 606/22; 128/400; 607/89, 104, 105

(56) References Cited

U.S. PATENT DOCUMENTS

| | | | |
|---|---|---|---|
| 3,425,419 A | * | 2/1969 | Dato .......................... 128/400 |
| 3,937,031 A | * | 2/1976 | Cook .............................. 62/98 |
| 5,334,181 A | * | 8/1994 | Rubinsky et al. .............. 606/22 |
| 5,609,619 A | * | 3/1997 | Pompei ....................... 607/104 |
| 5,878,582 A | * | 3/1999 | Appolonia et al. ............. 62/63 |
| 6,059,820 A | * | 5/2000 | Baronov ....................... 607/89 |
| 6,224,624 B1 | * | 5/2001 | Lasheras et al. ............ 607/105 |

* cited by examiner

Primary Examiner—Henry Bennett
Assistant Examiner—Sabrina Dagostino
(74) Attorney, Agent, or Firm—Daniel L. Dawes; Myers Dawes Andras & Sherman LLP

(57) ABSTRACT

The invention is a technique for dynamic measurements of the heat transfer coefficient to the outer layer of the skin surface using a high thermal conductivity metal in an insulating block as the standardized target. The coefficient is dependent on the specific design of the cryogen valve and nozzle, and values up to 11 500 W/m$^2$K values were measured for a 100 ms long spurts. The values for longer spurts are dependent on air humidity, as ice/snow formation then tends to form a thermally insulating layer. The average value of the heat transfer coefficient for a 200 ms long spurt was determined to 8000 W/m$^2$K for conditions of normal room humidity and temperature. The technique enables an improved prediction of the temperature profile and cooling efficiency during therapy, and may thereby contribute to an improved therapeutic outcome.

9 Claims, 6 Drawing Sheets

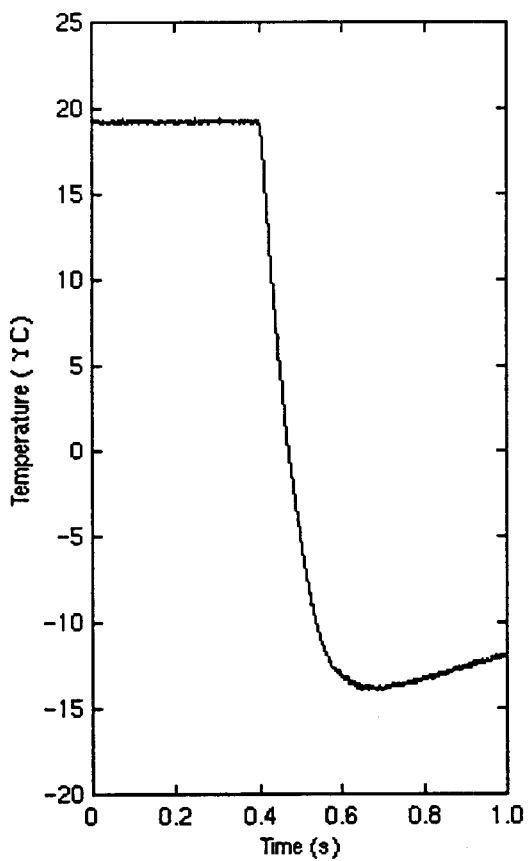 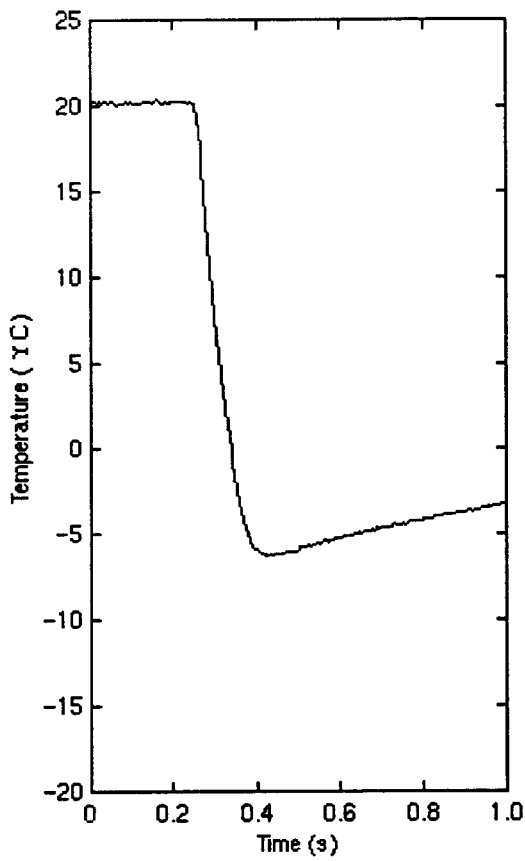
Fig. 4a                     Fig. 4b

METHOD AND APPARATUS FOR MEASURING THE HEAT TRANSFER COEFFICIENT DURING CRYOGEN SPRAY COOLING OF TISSUE

RELATED APPLICATION

The application is related to U.S. Provisional Patent Application, Ser. No. 60/178,529, filed on Jan. 25, 2000 and to U.S. Provisional Patent Application, Ser. No. 60/208,455, filed on May 31, 2000, which are both incorporated herein by reference.

BACKGROUND OF THE INVENTION

1. Field of the Invention

The invention relates to the field of laser therapy, and in particular, to the thermal treatment of biological tissues with laser radiation.

2. Description of the Prior Art

Laser induced selective photothermolysis is currently the preferred technique in treatment of many vascular disorders of the dermis. Typical examples are treatment of port wine stains and telangiectasia with short laser pulses in the green/yellow wavelength region. This light is strongly absorbed in hemoglobin whereas the absorption in other dermal constituents such as proteins and lipids are quite insignificant. The laser pulse is selected to be sufficiently long to allow heat to diffuse from the lumen to the entire vessel wall, but short enough to prevent thermal damage to perivascular structures.

Typical lasers currently being used in the clinic are flashlamp pumped dye lasers emitting at 585 nm wavelength and second-harmonic neodymium doped yttrium-aluminum-garnet lasers (Nd:YAG) at 532 nm. The pulse lengths are in the range of 0.5–1.5 ms.

However, thermal damage to the epidermis represents a severe problem that limits the acceptable power density of the laser beam. This is a general problem for laser therapy, because although the melanin absorption decays strongly with increasing wavelength, the absorption is significant over the entire visible and near-infrared part of the optical spectrum. Damage occurs when the epidermal temperature rises to about 70° C., i.e., about 35° C. above the normal temperature of 32–34° C.

These limitations can be significantly reduced if the epidermis is selectively precooled well below the normal temperature. Cooling of the epidermis to about 0° C. will allow for a 70° C. temperature rise, which corresponds to an increase in the maximum acceptable power density by a factor of about two. The maximum acceptable power density for a 585 nm laser used without cooling is in the range of 6–8 j/cm$^2$, whereas 15 J/cm$^2$ is routinely used with cooling at Beckman Laser Institute and Medical Clinic, such as disclosed in Nelson, et al., "*Apparatus And Method For Dynamic Cooling Of Biological Tissues For Thermal Mediated Surgery*," U.S. Pat. No. 5,814,040 (1998), which is incorporated herein by reference.

BRIEF SUMMARY OF THE INVENTION

The invention is a method of controlling temperature profiles of tissue subjected to cycles of cooling and heating comprising the steps of cooling the tissue and heating the tissue. The step of cooling the tissue is controlled according to a heat transfer coefficient referred to a tissue junction relative to a surface of the tissue subjected to cooling.

In the illustrated embodiment the tissue is skin having a stratum corneum and epidermis. However, it must be understood that any tissue, human or animal, is contemplated as being with the scope of the invention. The tissue junction in the case of the illustrated embodiment is an interface between the stratum corneum and epidermis. The step of cooling the tissue comprises the step of controlling cooling of the tissue according to an effective heat transfer coefficient between a cooling agent at the surface of the skin and the interface between the stratum corneum and epidermis.

The step of cooling is controllable by an amount of cooling applied to the tissue. The step of cooling the tissue according to the heat transfer coefficient comprises the step of varying the amount of cooling according to distance from the surface of the tissue to the tissue junction. In this way, for example, the cooling applied to various skin lesions is customized to the thickness of the lesion being treated. In particular in the illustrated embodiment, the step of cooling the skin according to the heat transfer coefficient comprises the step of varying the amount of cooling according to distance from the surface of the skin to the interface between the stratum corneum and epidermis.

The step of cooling the tissue is controlled according to a heat transfer coefficient is based on the step of determining the heat transfer coefficient using a thermally conductive metal target mounted in an insulating substrate as a standard which is exposed to the cooling.

In the illustrated embodiment the step of cooling comprises spraying cryogen droplets onto the tissue. However, any agent for cooling, now known or later devised, may be employed and the invention is not limited to cryogenic cooling.

The step of cooling the tissue is controlled according to a heat transfer coefficient is based on determining the heat transfer coefficient using a thermally conductive metal target mounted in an insulating substrate as a standard which is exposed to the cooling.

The invention is also characterized as an apparatus for performing the above method and the standard by which the heat coefficient is determined.

While the method has been described for the sake of grammatical fluidity as steps, it is to be expressly understood that the claims are not to be construed as necessarily limited in any way by the construction of "means" or "steps" limitations under 35 USC 112, but to be accorded the full scope of the meaning and equivalents of the definition provided by the claims. However, it is intended that the scope of the invention never be less than the scope of equivalency provided by 35 USC 112. The invention can be better visualized by turning now to the following drawings wherein like elements are referenced by like numerals.

BRIEF DESCRIPTION OF THE DRAWINGS

FIG. 3a is a linear in temperature and FIG. 3b is logarithmic in temperature.

FIGS. 4a and 4b are graphs of the temperature response as a function of time of a silver disk exposed to a 100 ms long cryogen spurt. Air humidity is 40%. FIG. 4a shows the graph for an applicator, GentleLase®" made by Candela Corp. and FIG. 4b shows the graph of an applicator, ScleroPLUS®', also made by Candela Corp.

In FIG. 5a air humidity is 40%. In FIG. 5b air humidity is 18%.

Figure 1:
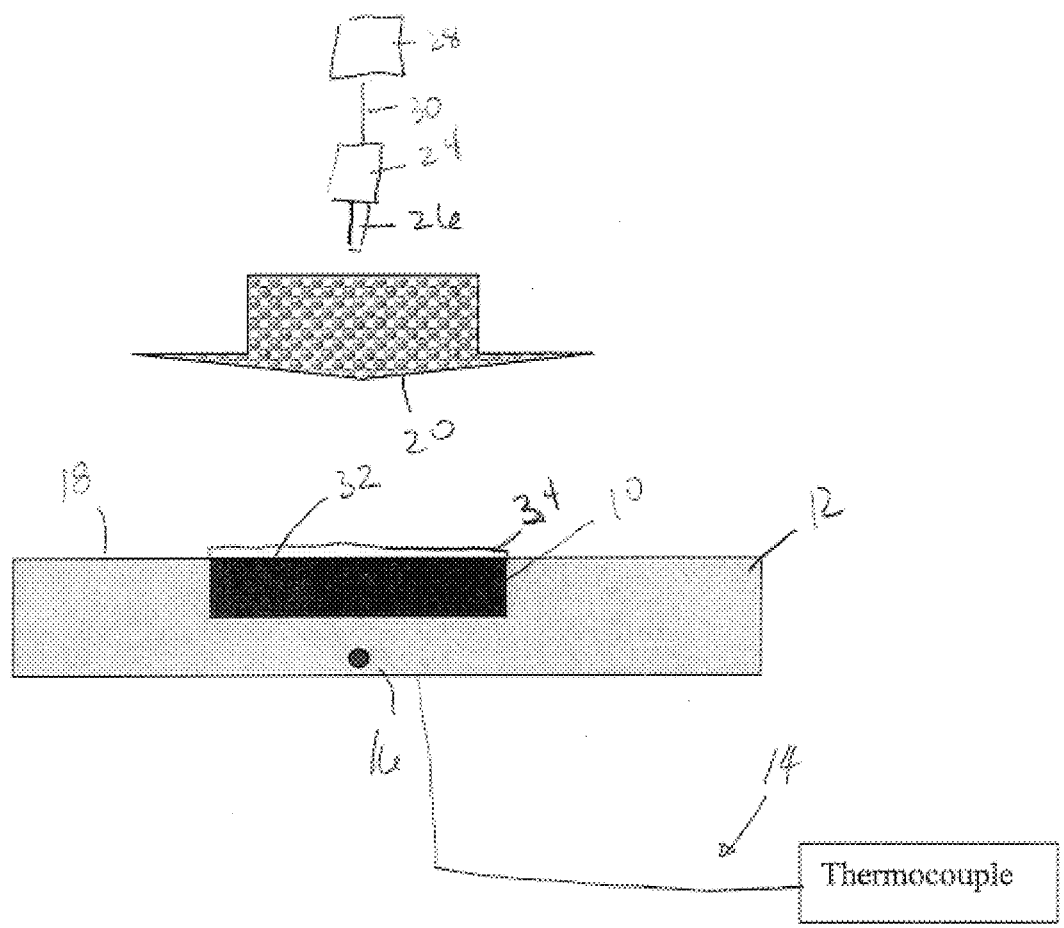
FIG. 1 is a simplified experimental setup for measuring high heat transfer coefficients.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Cryogen spray cooling has recently been developed for epidermal protection during laser-induced photothermolysis of port-wine stains. However, the prior art literature has no consistent values for the heat transfer coefficient at the skin surface. The only reported results are based on tissue phantoms, and values vary from 1600 to 60 000 W/m²K. The invention is a new technique for dynamic measurements of the heat transfer coefficient to the outer layer of the skin surface, i.e., the stratum corneum, with short spurts of atomized tetrafluoroethane. The coefficient is dependent on the specific design of the cryogen valve and nozzle, and values up to 11 500 W/m²K values were measured for a 100 ms long spurts. The values for longer spurts are dependent on air humidity, as ice/snow formation then tends to form a thermally insulating layer. The average value of the heat transfer coefficient for a 200 ms long spurt was determined to 8 000 W/m²K for conditions of normal room humidity and temperature. The technique enables an improved prediction of the temperature profile and cooling efficiency during therapy, and may thereby contribute to an improved therapeutic outcome.

Principles of Selective Cooling

Selective cooling of the epidermis according to the invention relies on two specific conditions:

1. Cooling takes place during a time interval corresponding to the thermal diffusion time across the epidermis; and
2. The heat transfer coefficient between the cooling agent and the skin should not be less than the thermal admittance of the epidermis.

The time, $\tau_e$, required for thermal diffusion through the epidermis is of the order of, $$\tau_e \approx \frac{d_e^2}{\chi} \qquad 1$$

where $d_e$ is the epidermal thickness and $\chi$ is the thermal diffusivity. The epidermal diffusion time for the human epidermis with a typical thickness of 60–100 μm and a diffusivity of $1.2 \cdot 10^{-7}$ m²/s is $\tau_e$=30–80 ms. The thermal resistance of the epidermis is given by, $$R_e = \frac{d_e}{\kappa} \qquad 2$$

where κ is thermal conductivity. The thermal resistance of the 60–100 μm thick epidermis with a thermal conductivity in the range of κ=0.2–0.4W/mK is thus $R_e$=1.5–5·10⁻⁴ m²K/W. The corresponding inverse quantity, i.e., the thermal admittance or the heat transfer coefficient is $H_e$=2000–6600 W/m²K.

Several methods of skin cooling have been developed, ranging from cooling with forced air and/or gas flow, contact cooling with an ice cube or another cold object, and cooling with liquid cryogen. However, the combined requirement of cooling during a 30–80 ms long period with a contact admittance larger than 2000–6600 W/m²K is difficult to achieve by any of these methods. Cooling by forced air with velocities of 1.5–15 m/s corresponding to a heat transfer coefficient in the range of H=10–60 W/m²K (CRC 1970), is a slow process. The time required for cooling the epidermis by 25% of the temperature difference between tissue and cold air flowing at 15 m/s is about 30 s. The temperature gradients in dermis will be small, and the port-wine stain vessels that are located at typically 200–400 μm will be cooled by 22–23%. Cooling of the upper dermis might be acceptable for treatment of deeply located targets, such as hair follicles, but it is unacceptable for port-wine stains vessels.

Cooling by flowing water will increase the heat transfer coefficient significantly. The heat transfer coefficient for turbulent water flow at 4° C. in a 50 mm diameter tube ranges from H=2000–12500 W/m²K for water velocities in the range from 0.6 to 6 m/s.

Cooling by contacting the skin with a cold solid medium, e.g., a sapphire disk is also an interesting technique. However, it might be difficult to contact the skin at sufficiently fast and time scale and accurately controlled contact durations.

The techniques of spraying the skin with 50–100 ms long spurts of liquid tetrafluoroethane (R134a) has been developed over the last few years. The duration of the spray is easily controlled with an electronic fuel injection valve. However, the value of the heat transfer coefficient between the spray and the skin has been very uncertain, and values over the broad range of H=1600–6000W/m²K have been reported.

In vivo measurement of a thermal distribution confined to the epidermal region is a very challenging task. The measurement of such steep thermal gradients with inserted thermocouples suffers, for example, severe limitations. The wire diameter of the smallest commercially available microthermocouple is 25 μm, and the corresponding bead diameter is 60 μm, which is about the same as the full epidermal thickness. The thermal conductivities of thermocouple metals are typically two to three orders of magnitude larger than that of tissue, and metallic thermocouples will therefore perturb the thermal distribution significantly. The readings of the thermocouple will only represent the tissue temperature when the thermal gradients have become sufficiently small. This will only occur when the thermal front has propagated deeply into the tissue, i.e., to a depth corresponding to several times the epidermal thickness. This phenomenon represents a problem for the measurement of high heat transfer coefficients since the contact resistance then becomes a very small fraction of the total resistance. The accuracy in measuring high heat transfer coefficient with this method is therefore quite problematic.

The same limitations are also relevant for measuring the heat transfer coefficient with tissue phantoms made of epoxy resin, which has thermal properties of about the same magnitude as those of tissue.

The surface heat transfer coefficient is, however, a surface phenomenon dependent on parameters such the velocity and size of the impinging droplets, the surface texture of the stratum corneum as well as on the chemical/physical properties of the cryogen and of the stratum corneum surface. The temperature drop between the spray and the skin surface takes place in a thin boundary layer. The transfer coefficient is only dependent on the properties within this layer and its boundaries, and it is independent on the subsurface properties of the stratum corneum and of the epidermis.

The storage of heat in such boundary layers is usually quite small, and this energy might therefore be neglected. To neglect the stored heat corresponds to assuming an infinitely large thermal diffusivity. In other words, it is assumed that heat propagates fast enough through the layer to ensure a quasi-steady state condition at all instants of time.

The flux of heat, $j_n$(W/m$^2$), from the outside to the tissue can then expressed, $$j_n = H(T_c - T) = \frac{T_c - T}{R_s} \qquad 3$$

where $T_c$, $T$ and $H$ are, respectively, the temperature of the cooling medium, the temperature of the skin surface and the heat transfer coefficient.

Principle of Measurements of High Heat Transfer Coefficients

Many of the problems associated with fast, accurate measurements of high heat transfer coefficients can be solved by using a metallic detector. The diffusion distance in, for example, pure silver is about 3 mm for the time corresponding to thermal diffusion through a 100 μm thick epidermis.

A simple experimental setup is shown in the block diagram of FIG. 1. A disk shaped thermal body 10 of a high thermal conductivity material, e.g., silver, is partly embedded in a good thermal insulator 12 such as, e.g., polystyrene foam. The temperature is monitored by a thermocouple 14 attached to the lower surface 16 of disk 12. The upper surface 18 is exposed to the liquid cryogen spray 20 with a beam diameter large enough to ensure uniform conditions across the disk 10.

The measurements will be done in a time scale where the temperature of the body 10 can be taken to be uniform, i.e., in a time scale satisfying, (Eq.1)

$$t \gg \frac{d_m^2}{\chi_m} \qquad 4$$

where the thickness and the thermal diffusivity of the disk 10 are, respectively, $d_m$ and $\chi_m$. The cooling of the metallic disk 10 can then be expressed, $$\rho_m C_m V_m \frac{dT}{dt} = A_m H(T_c - T) \qquad 5$$

where $\rho_m$, $C_m$, $V_m$, $A_m$ are, respectively, the specific gravity, the specific heat per unit mass, the volume, and the exposed surface area of the disk 10. The heat transfer coefficient is H, and T and $T_c$ are, respectively, the temperature of the disk 10 and the temperature of the cryogen spray 20. The solution of Eq.5 can be expressed, $$T = \Delta T\left(1 - e^{-\frac{t}{\tau_m}}\right) + T_n \qquad 6$$

where $$\rho_m C_m = \frac{\kappa_m}{\chi_m}$$

and $V_m = A_m d_m$ has been substituted, and where $\kappa_m$ and $$\tau_m = \frac{\kappa_m d_m}{\chi_m H}$$

are, respectively, the thermal conductivity and thermal relaxation time of the disk 10. The parameters $T_n$ and $\Delta T$ are, respectively, the initial temperature of the disk 10 and the temperature difference between the cryogen spray 20 and this initial temperature.

The temperature of the spray 20 and the heat transfer coefficient can thus be measured by monitoring the disk temperature during cooling. The temperature of the spray 20 is in principle given by the steady state temperature, i.e., $T(t\rightarrow\infty)=T_c$ and the heat transfer coefficient is given by the thermal relaxation time, $$H = \frac{\kappa_m d_m}{\chi_m \tau_m} \qquad 7$$

The determination of the heat transfer coefficient is only dependent on the dynamics of the cooling process, and it is therefore not necessary to let the initial disk temperature equalize with the ambient temperature between subsequent measurements.

A relevant geometry of the disk 10 might be a disk diameter equal to that of the width of the laser beam, together with a thickness of about 1 mm. The time required to equalize the temperature of a silver object of this thickness will be $$t \approx \frac{d_m^2}{\chi_m} = 5.9 \text{ ms } (\chi_m = 1.7 \cdot 10^{-4} \text{ m}^2/\text{s}),$$

which is 1400 times faster than required for a tissue sample of the same geometry. A relatively small heat transfer coefficient of H=2500W/m$^2$K corresponds to a thermal relaxation time of 1 s for the 1 mm thick silver disk ($\kappa_m$=425 W/mK), and a large transfer coefficient of H=25 000W/m$^2$K corresponds to a relaxation time of 100 ms. (Eq.7).

Emphasis should be given to ensure a good thermal contact between the thermocouple bead 14 and the silver disk 10, e.g., by micro soldering or welding. A poor thermal contact between the thermocouple bead 14 and the silver disk 10 will result in an additional thermal constant, which easily might be comparable to the relaxation time of the disk 10 itself.

Small heat transfer coefficients result in long relaxation times, and it might then be necessary to correct for heat loss into thermal insulation 12. Heat propagates a distance of $\sqrt{\chi_i t}$ in the insulation 12 during the interval of time t. The ratio between thermal energy supplied by the insulation 12 during a cooling period and the energy simultaneously taken from the silver disk 10 can be approximated (Eq.1), $$F \approx \frac{\rho_i C_i \sqrt{\chi_i t}}{\rho_m C_m d_m} \qquad 8$$

where $\rho_i C_i$ is the specific heat per unit volume of the insulating material, and $\chi_i$, is its thermal diffusivity.

The thermal conductivity of insulating foam materials is rather close to that of air, i.e., $\kappa_i$=25 mW/m·K. The specific heat is in the range of $\rho_i C_i$=25 kJ/m$^3$ and the corresponding thermal diffusivity is $\chi_i$=1·10$^{-6}$ m$^2$/s. Thus, the fractional thermal energy supplied by the foam to a 1 mm thick silver disk 10 will be about 0.3% over a period of 100 ms. The thermal diffusivity and conductivity of epoxy resin are, respectively, $\chi_i$=1.1·10$^{-7}$ m$^2$/s and $\kappa_i$=0.14W/mK. The fraction F will then be about 5% for the 100 ms period.

Measurements of the heat transfer coefficient between the cryogen spray 20 and other materials than silver can be done by covering the disk 10 with a very thin layer of the actual material. This layer introduces an additional thermal resistance, and the heat transfer coefficient, H, can be found from the measured value, H*, $$H = \frac{H_l H^*}{H_l - H^*} \qquad 9$$

where $H_l = \kappa_l / d_l$ is the thermal admittance for a layer of thickness $d_l$ with a thermal conductivity $\kappa_l$. This expression applies, of course, only if the heat transfer time across the layer is much less than that for the metal disk, i.e., (Eq.1)

$$d_l << \sqrt{\frac{\chi_l}{\chi_m}} d_m \qquad 10$$

The thermal diffusivity of silver is more than thousand times larger the value for most organic materials, and this condition therefore requires that the layer thickness should be much less that 3–4% of the disk thickness. Thus, an organic layer of 5–10 $\mu$m thickness should be quite acceptable for a 1–2 mm thick disk 10.

Results

A measuring setup was made in accordance with FIG. 1. The measuring disks 10 were machined from 99.9% pure silver. In order to obtain a surface roughness corresponding to that of the skin the exposed surface 16,18 was brushed with a fine steel wire brush. All disks 10 were manufactured with 10 mm diameter, with thickness ranging from 0.7 mm to 2 mm.

The disks 10 were for practical reasons embedded in epoxy resin 12. The thermocouples 14 were of Chromel-Alumel type with 130 $\mu$m wire diameters. The 300 $\mu$m diameter bead was in part soft-soldered to the disk 10 (60% Sn and 40% Pb). The accuracy of the thermocouple 14 was controlled by measuring steady state temperatures with an identical thermocouple 14 attached to the disk 10 with heat conductive paste. Contacting with thermal paste introduced, due to the limited thermal conductivity of the thermal paste, an additional time constant of about 50 ms.

The cryogen spray 20 (tetrafluoroethane, R134$a$) was controlled with a standard automotive fuel injection valve 24 for gasoline engines (Borg Warner® Injector #57031). The valve 24 was connected to a container 28 of liquid cryogen via a high-pressure hose 30. The container 28 was mounted upside down in order to feed liquid cryogen into the valve 24. The container 28 was held at room temperature, which corresponds to a pressure of 670 kPa at 25° C. The boiling point of R134$a$ is −26.1° C. at 1 atm. The finely dispersed spray of cryogen droplets had a conical geometry with an opening angle of 17°. The spray diameter at the detector disk 10 positioned at 50 mm distance from the nozzle 26 was then 15 mm.

The measurements of the cryogen spray temperature, which in principle could be measured as the steady state value for the detector 22 of FIG. 1, experienced problems with ice/snow formation for exposure times larger than a few hundred milliseconds. The temperature was therefore measured with a naked 300 $\mu$m bead diameter thermocouple 14 inserted directly in the cryogen spray 20. This detector 22, which is fast enough to measure the temperature before deposition of snow, measured a temperature of −50° C. at a distance of 50 mm from the nozzle 26. This temperature was due to evaporation and adiabatic expansion, well below the boiling point. See FIG. 2 which is a graph of spray temperature as a function of distance from nozzle 26 at two different nozzle sizes.

Measurements were carried of with either a freely exposed silver surface 32 or a disk covered with a layer of human stratum corneum 34. The attachment of the stratum corneum layer 34 was performed by first depositing a very thin layer of low viscosity ethylcyanoacrylate glue at the disk surface 32. The disk 10 was then strongly pressed (~100 kPa) against in vivo human skin for about 30 s. Pulling the disk 10 off the skin resulted in detachment of stratum corneum layer 34 from the epidermis as the layer was firmly glued to the silver surface 32. The technique thus yields a surface layer 34 on the disk 10 with a texture and chemical/physical properties as those of human skin. It is therefore expected that this model is quite representative for the surface of in vivo human skin, as the only difference is that the stratum corneum layer 34 is mounted upside down.

The thickness of female human stratum corneum 34 is reported to a mean value of 12.7 $\mu$m±4.2 $\mu$m for human extremities and 7.7 $\mu$m±1.8 $\mu$m for the abdomen. The thermal conductivity of the stratum corneum 34 was taken to be 0.2 W/mK, i.e., about the same as for keratinous fibers ($\kappa_{wool}$=0.18W/mK).

The results given in Table 1 below are based on a stratum corneum layer 34 detached in vivo from the flexor surface of the male forearm. The disk surface 32 was optically inspected to ensure a continuous stratum corneum layer 34, and the total layer thickness was measured to about 10 $\mu$m. It will usually not be required to correct for a 1–2 $\mu$m thick adhesive layer between the stratum corneum 34 and the silver surface 32 because the thermal conductivities of acrylic and keratinous materials are about the same. The upper data row gives the result based on measurement of the thermal relaxation time for a disk 10 with a free silver surface 32. The middle row gives the corresponding results for the same disk 10 covered with the stratum corneum layer 34. These latter values thus correspond to an effective heat transfer coefficient, H*, referred to the stratum corneum/silver interface 32/34. The lower row gives the heat transfer coefficient of the cryogen spray/stratum corneum interface 20/34 based on the values from the stratum corneum/silver interface 32/34, but transformed to the surface by correcting for the heat admittance of the stratum corneum layer 34 as given in Eq.9.

The first data column gives the heat transfer coefficient averaged over the first 100 ms of exposure, and the last column gives the corresponding value for 200 ms. The differences between the values in these two columns represent the impact of snow formation. No snow formation was observed for exposure times less than 100 ms, but onset of snow formation was observed soon after 100 ms for normal room air humidity (See also FIG. 5). The values given in Table 1 are based on the average of several series of measurement. The results were very reproducible with a typical deviation from the mean value of less than 10%.

TABLE 1

| Disk 10 | Heat Transfer coefficient Average over first 100 ms | Heat Transfer coefficient Average over first 200 ms |
|---|---|---|
| Silver surface 32 | H = 11000 W/m$^2$K | H = 7 900 W/m$^2$K |
| Stratum corneum covered surface, measured value | H* = 7 300 W/m$^2$K | H* = 5 700 W/m$^2$K |
| Stratum corneum 34 | H = 11 500 W/m$^2$K | H = 8 000 W/m$^2$K |

Spray characteristics: distance from nozzle 26 to disk 10 was 50 mm, opening angle of spray 17°, temperature −50° C. Stratum corneum layer 34: thickness 10 μm, thermal conductivity 0.2 W/mK (thermal admittance 20 000 W/m$^2$K).

The results given in Table 1 demonstrate that the heat transfer coefficients between the cryogen spray 20 and a silver surface 32 are very close to the values for spraying the stratum corneum 34. The results from spraying a silver surface 32 are therefore expected to be quite representative for the corresponding values in the case of actual skin cooling.

An opening angle of 17° is somewhat large for clinical applications where the diameter of the irradiated spot typically is 10 mm or less. The opening angle was reduced by mounting a stainless steel nozzle 26 with a cylindrical bore on the valve. Two different nozzles 26 were used, one with 0.7 mm bore diameter and the other with 1.4 mm. The nozzles 26 had the same length of 32 mm. These nozzles 26 confined the cryogen to the disk 10, but the diameter of the spray cone itself was somewhat smaller than the disk diameter. The transversal uniformity of the spray 20 was therefore reduced.

In order to get precise information of the dynamics of the cooling process, measurements were also done with a faster detector 22. This detector 22 had a disk thickness of 0.7 mm corresponding to a disk relaxation time of $\tau_m$=130 ms for a heat transfer coefficient in the range of H=10 000 W/m$^2$K. This relaxation time corresponds to a fractional amount of 9% of thermal energy delivered by the epoxy resin 12 (Eqs.7 and 8). The detector 22 had a free silver surface 32, which according to the results given in Table 1, should be quite representative for human skin. All the subsequent measurements were done with this detector design.

Figure 2:
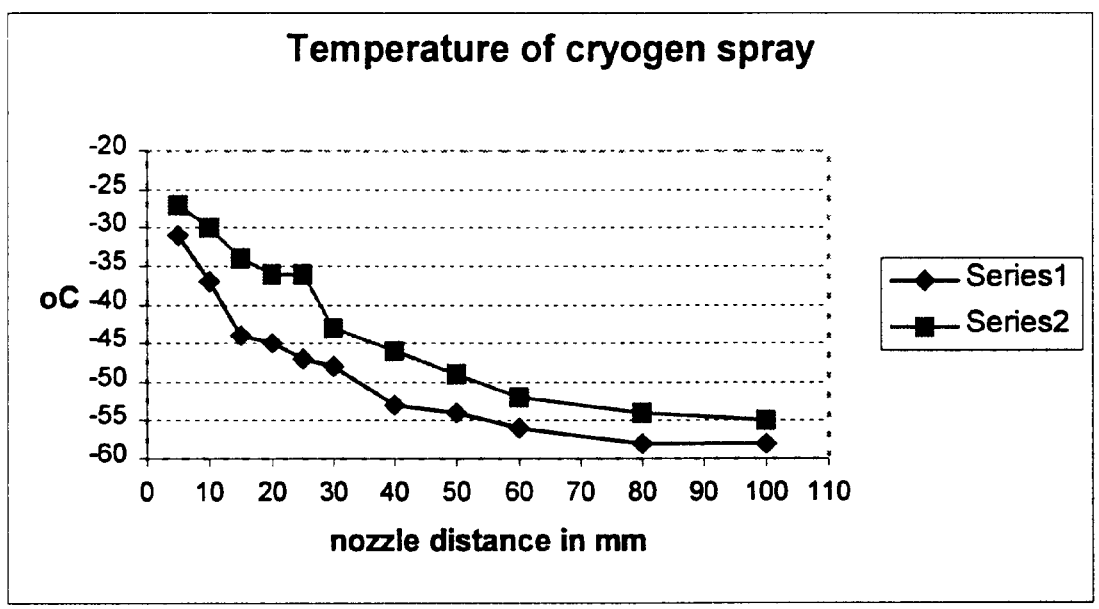
FIG. 2 is a graph of the longitudinal temperature distribution along a cryogen spray axis with a 0.7 mm bore nozzle and a 1.4 mm bore nozzle.

The spray temperatures were determined at a distance of 55–60 mm from the nozzle 26. The measured values were in the range of −50° C. to −55° C., and the lowest temperatures were found for the 0.7 mm bore nozzle 26. Typical thermal distributions for the two different nozzles 26 are shown in FIG. 2

Figure 3A:
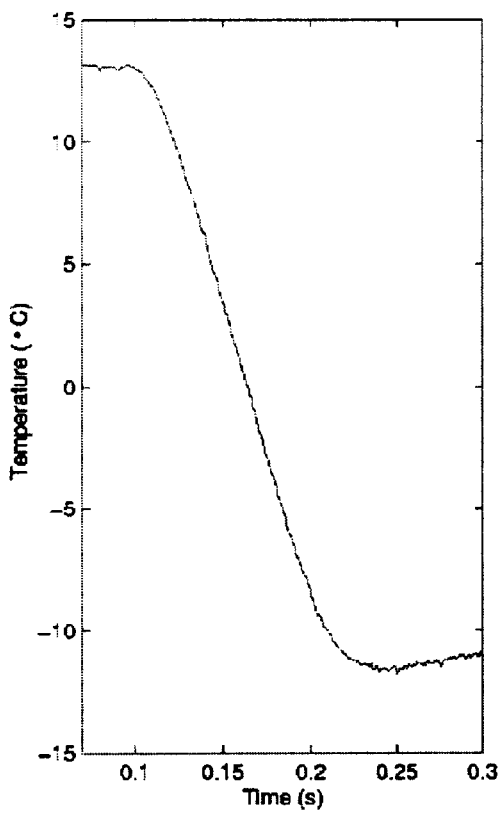
FIGS. 3a and 3b are graphs of the temperature response as a function of time of a silver disk exposed to a 100 ms long cryogen spurt. The valve opens at time 0.1 s and closes at 0.2 s. The nozzle bore is 0.7 mm. The distance between disk and nozzle is 55 mm. The air humidity is 40%.
Figure 3B:
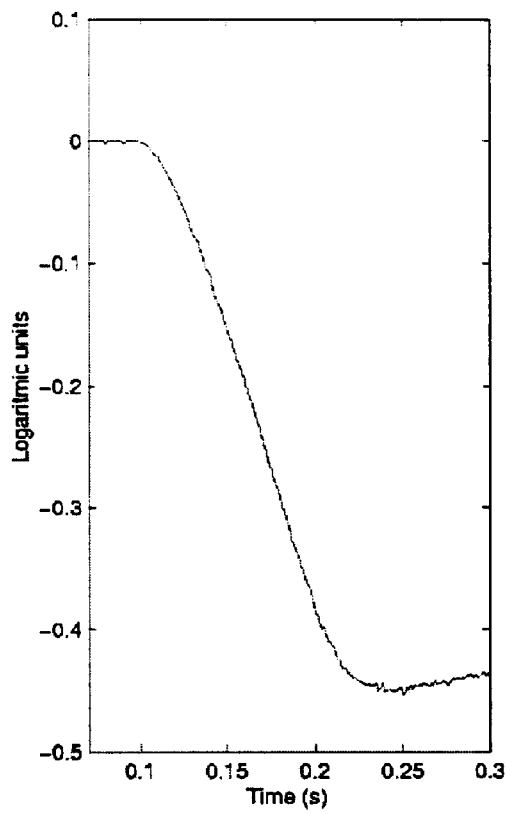

An example of temperature response of the silver disk 10 during a 100 ms long spurt is shown in FIGS. 3a and 3b. The continued decrease in temperature for another 50 ms after the end of the spurt is due to evaporation of a cryogen layer deposited at the disk surface 32. FIG. 3a shows a linear plot in temperature. In order to verify that the time constant does not vary during the spurt, a corresponding logarithmic plot is given in FIG. 3b. This plot displays the function ln((T−T$_c$)/(T$_n$−T$_c$)) vs. time for T$_n$=13.5° C. and T$_c$=−55° C. The logarithmic plot falls on an almost straight line during the spurt, thus demonstrating a non-varying time constant. The heat transfer coefficient for this case was determined to be H=7600 W/m$^2$K and to H=8200 W/m$^2$K when corrected for heat diffusing from the insulation during measurement.

The averaged values of the heat transfer determined for several measurements for each nozzle 26, and the typical variations were within 10%. The average values for a 100 ms long exposure were H=7200 W/m$^2$K the 0.7 mm bore nozzle 26, and H=10800 W/m$^2$ K for the 1.4 mm bore.

Measurements were also done on commercial equipment for cryogen cooling, namely the Dynamic cooling device DCD® from Candela Corp. The cryogen is here medical grade tetrafluoroethane (DuPont Dymel® 134a/P) and the container 28 is kept at a temperature slightly above room temperature. The container 28 is connected via a hose 30 to a hand-piece (not shown) where the cryogen valve 24 and nozzle 26 are mounted. Two different hand-pieces were tested, ScleroPLUS® and GentleLase®, both made by Candela Corp. The distance from these valves 24 to the silver disk 10 were as specified by the manufacturer for skin cooling.

The heat transfer coefficients for two hand pieces are shown in FIGS. 4a and 4b were found to be H=7400 W/m$^2$ K for the GentleLase® and H=6600 W/M$^2$ K for the, ScleroPLUS®. Both these values are thus close to the average value of H=7200 W/m$^2$ K found for the 0.7 mm bore nozzle 26.

Air humidity was varied from about 15% to 45%, but no significant changes in the heat transfer coefficients were found during a 100 ms long cryogen spurt. However, the humidity was of importance for longer spray duration. This is demonstrated in FIGS. 5a and 5b, which give the results for a 1 s spurt duration at, respectively, normal air humidity and dry air of 18% humidity.

Figure 5A:
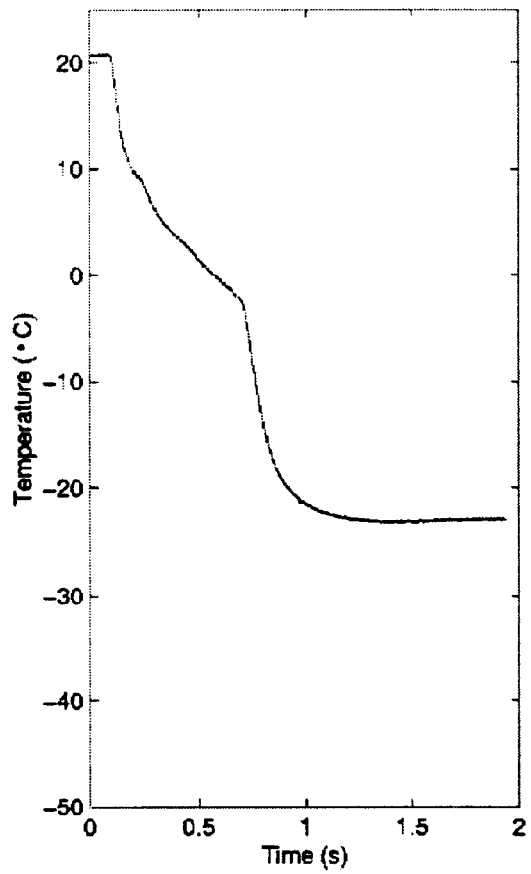
FIGS. 5a and 5b are graphs of the temperature response as a function of time of a silver disk exposed to a 1 s long cryogen spurt. The nozzle bore is 0.7 mm and the distance between the disk and nozzle was 55 mm.
Figure 5B:
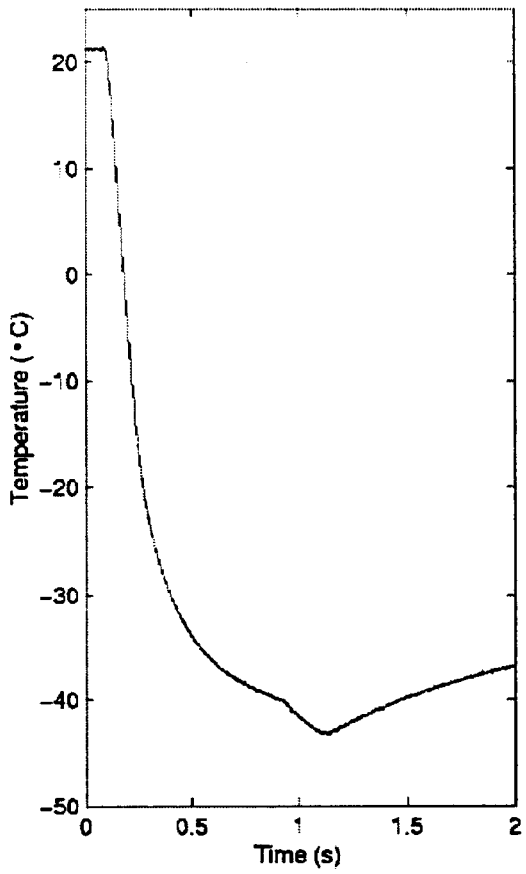

In the case of FIG. 5a snow formation was observed on the disk 10 after about 100 ms, but continued spray generated a slurry layer consisting of snow crystals and liquid cryogen. This layer remained visual at the surface 32 for more than 1 s after the spray, and the temperature remained almost constant at −23° C., i.e., close to boiling point of the cryogen. A tendency to snow formation, but much less pronounced, was also observed for reduced humidity as shown in FIG. 5b. The average transfer coefficient for the first 0.5 s was in this last case H=5800 W/m$^2$K.

Discussion

The heat transfer coefficient of the stratum corneum 34 has been determined to be about H=11 500 W/m$^2$K for a 100 ms long cryogen spurt. This value is well above the value for the epidermal thermal admittance of H$_e$=2000–6600 W/m$^2$K. The knowledge of the heat transfer coefficient enables calculation of the epidermal temperature profile.

Values for in vivo measurements of human skin has been reported to 0.39 W/mK. The thermal properties of the skin are dependent on the protein, lipid and water content. Since the thermal conductivity of water, i.e., 0.6 W/mK is about three times larger the value for keratinous fibers, it is expected that the conductivity increases gradually from the in vivo stratum corneum to the basal layer. However, the present calculation is based on a model where the in vivo stratum corneum is taken as a 10 μm thick layer with thermal conductivity of 0.2 W/mK, whereas the epidermal/dermal region is considered as a semi-infinite large medium with a thermal conductivity of 0.4 W/mK and a diffusivity of 1.2·10$^{-7}$ m$^2$/s.

The model does not take into account possible changes in the thermal properties from ice formation in the epidermal granular layer. Formation of ice will slow down the cooling process somewhat. However, it is certainly a possibility that epidermal tissue water can be supercooled to the calculated temperatures for the short duration of 50–100 ms.

Figure 6:
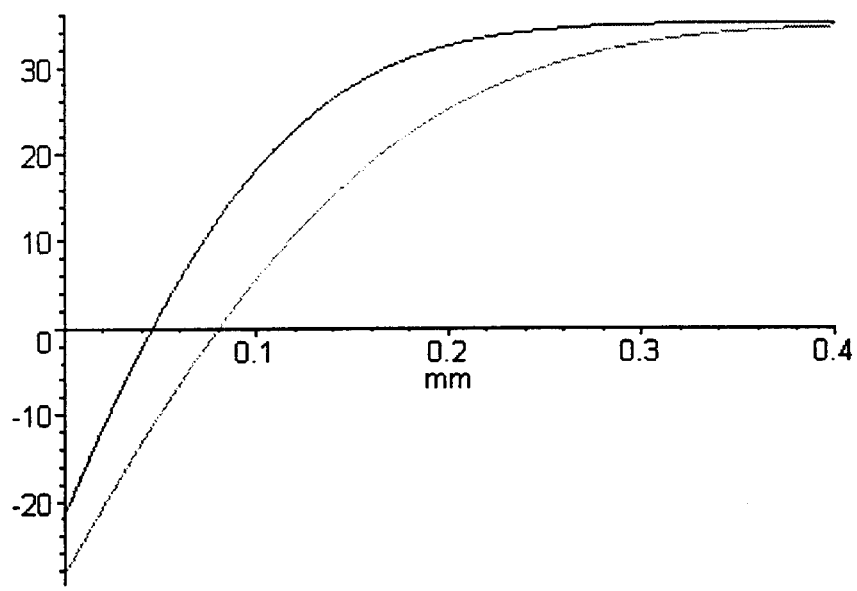
FIG. 6 is a graph of calculated temperature distribution in epidermis and upper dermis as a function of distance from the stratum corneum/epidermal junction. The temperature is taken immediately after a cryogen spurt. H*=7300 W/m2K and Tc=−50° C. The upper curve corresponds to a 50 ms spurt and the lower curve corresponds to a 100 ms spurt.

The temperature distributions in epidermis and upper dermis are illustrated in the graph of FIG. 6. (Eq. A4). The presence of the in vivo stratum corneum layer is accounted for by using the heat transfer coefficient H*, which refers to the effective heat transfer coefficient between the cryogen spray 20 and the in vivo stratum corneum/epidermal junction. The calculation is based on a value of H=7300 W/m²K, corresponding to a value of H=11500 W/m²K for the skin surface (See Table 1).

The upper curve and lower curves give, respectively, the thermal distribution after 50 ms and 100 ms. The calculations demonstrate that the a 50–100 ms cryogen spurt will selectively bring the in vivo epidermal temperature to values below to 0° C. whereas cooling of ectactic vessels typically located at 200–400 μm depth will be quite negligible.

In any given example the thermal profile can be calculated given the coefficient of heat transfer. The heat flux in a thermally conductive medium is proportional to the thermal gradient, $$\vec{j} = -\kappa \mathrm{grad} T \qquad \mathrm{A1}$$

where $\vec{j}$ is the heat flux vector, T is the temperature rise and κ is the thermal conductivity.

Conservation of energy requires that net flux of heat out of a unit volume, i.e., div $\vec{j}$, corresponds to change in stored thermal energy, $$\mathrm{div}\,\vec{j} = -\frac{\partial \rho C T}{\partial t}$$

where ρ and C are, respectively, the specific gravity and the specific heat per unit mass. The radiative boundary condition assumes that the flux of heat into the medium, $j_n$, is proportional to the temperature difference, ΔT, between the surrounding medium and that at the tissue surface, $$j_n = H \cdot \Delta T \qquad \mathrm{A3}$$

The solution of Eqs. A1–3 for a semi-infinite medium can be expressed, $$T(x,t) = \left( \mathrm{erfc} \frac{x}{2\sqrt{\chi_i t}} - e^{\frac{H}{k_t}x + \left(\frac{H}{k_t}\right)^2 \chi_i t} \mathrm{erfc}\left( \frac{x}{2\sqrt{\chi_i t}} + \frac{H}{k_t}\sqrt{\chi_i t} \right) \right) \Delta T + T_n \qquad \mathrm{A4}$$

where x is the distance from the surface and $T_n$ is the normal tissue temperature.

Conclusion

The described techniques for dynamic measurements of the heat transfer coefficients during cryogen cooling yields reproducible and accurate values. The transfer coefficient during a 100 ms long spurt of tetrafluoroethane onto the in vivo stratum corneum was determined to 11 500 W/m²K. The value of the coefficient is well above the thermal admittance of the in vivo epidermis, and thus near optimal for epidermal protection during laser therapy of port-wine stains.

The technique also enables measurement of an effective heat transfer coefficient between the cryogen spray 20 and the in vivo stratum corneum/epidermal junction. The use of a heat transfer coefficient referred to this junction enables the cooling conditions to be corrected for the thickness of the in vivo stratum corneum of each individual lesion. In a clinical situation this will ensure that the heat transfer coefficient is determined for the specific lesions, and thereby possibly contribute to improvement of the treatment protocol.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method of controlling temperature profiles of tissue subjected to cycles of cooling and heating comprising:
    cooling said tissue; and
    heating said tissue, where cooling said tissue is controlled according to a measurement of a simulated heat transfer coefficient referred to a tissue junction relative to a surface of said tissue subjected to cooling.

2. The method of claim 1 where said tissue is skin having a stratum corneum and epidermis, said tissue junction being an interface between said stratum corneum and epidermis and where cooling said tissue comprises controlling cooling of said tissue according to an effective heat transfer coefficient between a cooling agent at said surface of said skin and said interface between said stratum corneum and epidermis.

3. The method of claim 1 where cooling is controllable by an amount of cooling applied to said tissue, and where cooling said tissue according to said heat transfer coefficient comprises varying said amount of cooling according to distance from said surface of said tissue to said tissue junction.

4. The method of claim 2 where cooling is controllable by an amount of cooling applied to said skin, and where cooling said skin according to said heat transfer coefficient comprises varying said amount of cooling according to distance from said surface of said skin to said interface between said stratum corneum and epidermis.

5. A method of controlling temperature profiles of tissue subjected to cycles of cooling and heating comprising:

cooling said tissue; and heating said tissue, where cooling said tissue is controlled according to a heat transfer coefficient is based on determining said heat transfer coefficient using a thermally conductive metal target mounted in an insulating substrate as a standard which is exposed to said cooling.

6. The method of claim 1 where said cooling comprises spraying cryogen droplets onto said tissue.

7. The method of claim 5 where said cooling comprises spraying cryogen droplets onto said tissue.

8. A method of controlling temperature profiles of tissue subjected to cycles of cooling and heating comprising:

cooling said tissue; and heating said tissue, where cooling said tissue according to said heat transfer coefficient comprises varying said amount of cooling according to distance from said surface of said tissue to said tissue junction, and where cooling said tissue is controlled according to a heat transfer coefficient is based on determining said heat transfer coefficient using a thermally conductive metal target mounted in an insulating substrate as a standard which is exposed to said cooling.

9. A method of controlling temperature profiles of tissue subjected to cycles of cooling and heating, where said tissue is skin having a stratum corneum and epidermis, said tissue junction being an interface between said stratum corneum and epidermis, comprising:

cooling said tissue; and heating said tissue, where cooling said tissue comprises controlling cooling of said tissue according to an effective heat transfer coefficient between a cooling agent at said surface of said skin and said interface between said stratum corneum and epidermis, where cooling is controllable by an amount of cooling applied to said skin, where cooling said skin according to said heat transfer coefficient comprises varying said amount of cooling according to distance from said surface of said skin to said interface between said stratum corneum and epidermis, and where cooling said tissue is controlled according to a heat transfer coefficient is based on determining said heat transfer coefficient using a thermally conductive metal target mounted in an insulating substrate as a standard which is exposed to said cooling.

* * * * *

UNITED STATES PATENT AND TRADEMARK OFFICE
CERTIFICATE OF CORRECTION

PATENT NO.    : 6,669,688 B2
DATED         : December 30, 2003
INVENTOR(S)   : Lars O. Svaasand et al.

It is certified that error appears in the above-identified patent and that said Letters Patent is hereby corrected as shown below:

Drawings,
Please replace Fig. 1 as follows:

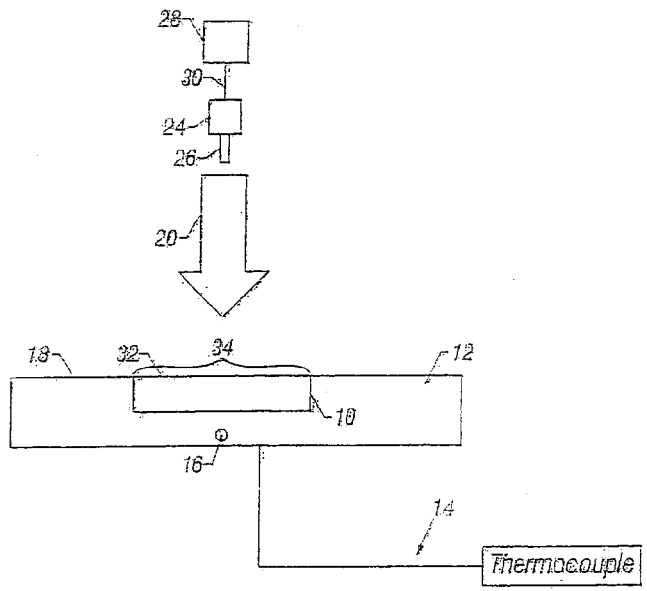

Signed and Sealed this

Twenty-fourth Day of August, 2004

JON W. DUDAS
*Director of the United States Patent and Trademark Office*